United States Patent [19]
Carduck et al.

[11] Patent Number: 5,324,871
[45] Date of Patent: Jun. 28, 1994

[54] HYDROGENATION PROCESS

[75] Inventors: Franz-Josef Carduck, Haan; Gerd Goebel, Cologne; Theo Fleckenstein, Hilden; Udo Kreutzer, Monheim; Guenther Demmering, Solingen-Graefrath, all of Fed. Rep. of Germany

[73] Assignee: Henkel Kommanditgesellschaft auf Aktien, Duesseldorf, Fed. Rep. of Germany

[21] Appl. No.: 920,439

[22] PCT Filed: Feb. 13, 1991

[86] PCT No.: PCT/EP91/00277

§ 371 Date: Oct. 21, 1992

§ 102(e) Date: Oct. 21, 1992

[87] PCT Pub. No.: WO91/13050

PCT Pub. Date: Sep. 5, 1991

[30] Foreign Application Priority Data

Feb. 22, 1990 [DE] Fed. Rep. of Germany ....... 4005629

[51] Int. Cl.$^5$ ............................................. C07C 27/04
[52] U.S. Cl. ...................... 568/884; 568/885; 554/143
[58] Field of Search .................. 568/885, 884; 554/143

[56] References Cited

U.S. PATENT DOCUMENTS

| | | | |
|---|---|---|---|
| 4,804,790 | 2/1989 | Schuett | 568/885 |
| 4,942,266 | 7/1990 | Fleckenstein et al. | 568/864 |
| 5,043,485 | 8/1991 | Fleckenstein et al. | 568/885 |
| 5,124,491 | 6/1992 | Fleckenstein et al. | 568/885 |

*Primary Examiner*—Jose' G. Dees
*Assistant Examiner*—Dwayne C. Jones
*Attorney, Agent, or Firm*—Ernest G. Szoke; Wayne C. Jaeschke; Daniel S. Ortiz

[57] ABSTRACT

The invention relates to a process for the hydrogenation of native fats, oils and fat derivatives, such as fatty acids and fatty acid esters, to fatty alcohols in a fixed-bed reactor, more particularly in co-current, hydrogen being recirculated in a stoichiometric excess, more particularly in an excess of 10 to 100 fold, and the fat, oil or fat derivative passing through the reactor only once. To minimize the specific hydrogen demand without having to accept significant losses in regard to specific reactor load, product selectivity and catalyst life, the hydrogen is passed successively through at least two fixed-bed reactors 4,10 without the gas issuing from the reactors 4 and entering the following reactors 10 being cooled and the fat, oil or fat derivative is simultaneously introduced into the reactors 4,10.

4 Claims, 5 Drawing Sheets

HYDROGENATION PROCESS

FIELD OF THE INVENTION

This invention relates to a process for the hydrogenation of native fats, oils and fat derivatives, such as fatty acids and fatty acid esters, to fatty alcohols in a fixed-bed reactor, more particularly in co-current, hydrogen being recirculated in a stoichiometric excess, more particularly in an excess of 10 to 100 fold, and the fat, oil or fat derivative passing through the reactor only

RELATED ART

In a known process of this type, for example for the hydrogenation of fatty acid methyl ester, the actual hydrogenation reaction takes place in one or more fixed-bed reactors arranged in tandem at temperatures in the range from 200° to 250° C. and under a hydrogen pressure of 200 to 300 bar. To this end, the fatty acid methyl ester is pumped under pressure into the plant where it is mixed with compressed hydrogen, heated with the compressed hydrogen to the reaction temperature and introduced into the reactor from above.

After passing through the reactors, the reaction mixture is cooled and separated in a separator into the liquid phase and the gas phase. The liquid phase is expanded and delivered to the methanol separation unit while the gas phase, which consists mainly of hydrogen, is recirculated via a compressor. In the methanol separation unit, which is in the form of an evaporator, the fatty alcohol is freed from the methanol and may then be used for its intended purpose without further purification.

However, the catalytic hydrogenation of fats, oils and fat derivatives to fatty alcohols in a fixed-bed reactor (trickle-bed method), particularly under adiabatic conditions, requires a large excess of hydrogen of 10 to 100 times the stoichiometric quantity to ensure that a large part of the heat of reaction is dissipated through the large excess of gas. This is because excessive temperatures in the catalyst bed lead increasingly to secondary products and shorten the life of the catalyst.

In industrial plants, the hydrogen is recirculated for economic reasons. To this end, the hydrogen has to be cooled to around 50° C. after passing through the reactor at 230° C., compressed by the recycle gas compressor and reheated to the reaction temperature in a peak heater. The economy of a hydrogenation process such as this in regard to capital investment and operating costs is thus largely determined by the specific recycle gas demand ($Nm^3$ $H_2$/t reaction product).

Accordingly, the problem addressed by the present invention was to minimize the specific hydrogen demand by process measures without significant losses having to be accepted in regard to the specific reactor load, product selectivity and catalyst life.

SUMMARY OF THE INVENTION

According to the invention, the solution to this problem for a process of the type mentioned at the beginning is characterized in that the hydrogen is passed successively through, at least, two fixed-bed reactors without the gas issuing from the reactors and entering the following reactors being cooled and in that the fat, oil or fat derivative are simultaneously introduced into the reactors.

The process according to the invention may be carried out irrespective of the particular type of reactor used, for example a shaft reactor or tube bundle reactor, and irrespective of its method of operation, for example adiabatic or isothermal. In hydrogenation plants comprising n reactors, the specific recycle gas volume is reduced to 1/n. The accumulation of volatile components in the gas phase leads to only a slight loss of performance of the order of 5 to 10% for the second reactor and the following reactors. Neither the selectivity nor the useful life of the catalyst is significantly affected.

In another embodiment, the process is carried out using two reactors.

In another advantageous embodiment of the process according to the invention, the liquid reaction products are removed from the gas issuing from the preceding reactors before the gas enters the following reactor. It is of particular advantage in this regard if the liquid reaction products separated from the gas are introduced into the gas issuing from the last reactor, cooled together with the gas, separated into a liquid phase and a gas phase and the gas phase is subsequently returned to the first reactor.

The present invention also relates to a plant for the hydrogenation of starting products consisting of fats, oils and fat derivatives, such as fatty acid and fatty acid ester, to fatty alcohols, comprising at least one fixed-bed reactor through which the starting product and the hydrogen are passed, heaters preceding the reactor for the starting product and the hydrogen, a cooling system for the reactor outflow and a following separator for gas/liquid separation which is connected to the reactor for recirculating the gas.

In this plant, the problem addressed by the invention is solved by at least two fixed-bed reactors arranged in tandem which are connected to one another by a separator of which the liquid outflow is conducted to the outflow of the last reactor and by a parallel feed line for delivering the starting product to each of the reactors.

In one advantageous embodiment, there are two fixed-bed reactors arranged in tandem.

In one particular embodiment, each feed line for the starting product comprises a pump and a heat exchanger. In this way, the quantity and temperature of the feed for each reactor can readily be separately adjusted.

BRIEF DESCRIPTION OF THE DRAWINGS

Examples of embodiment of the invention are described in detail in the following with reference to the accompanying drawings, wherein.

DETAILED DESCRIPTION OF THE INVENTION

Embodiments of the process according to the invention were carried out in a 2×20 liter double reactor plant. Coconut oil was directly hydrogenareal with formation of fatty alcohols and 1,2-propanediol.

Figure 1:
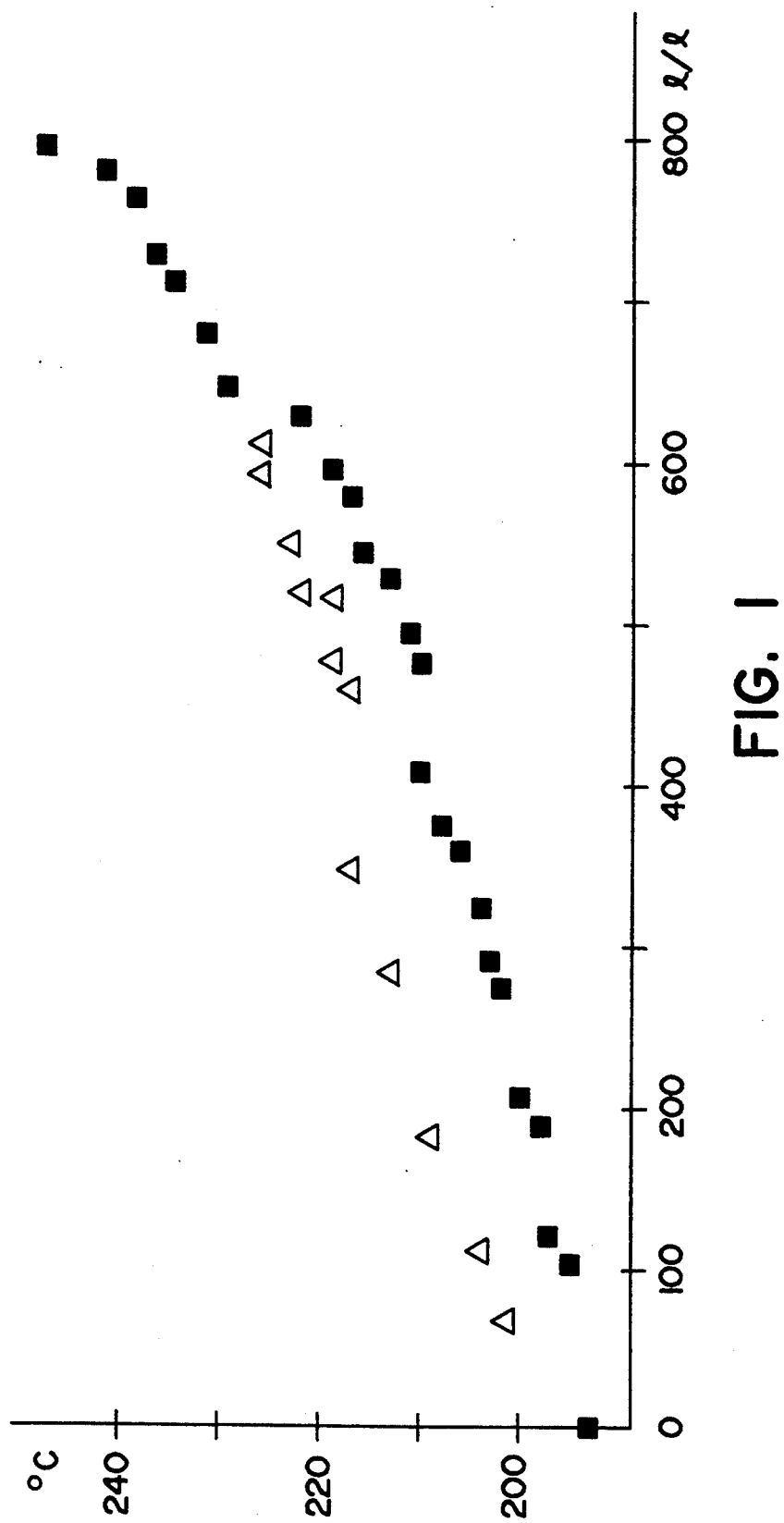
FIG. 1 shows the catalyst load in the form of a graph in which the temperature is plotted against the ratio of feed volume to catalyst volume.

FIG. 1 shows the results in regard to catalyst life in the process according to the invention operated with an LHSV of 0.71 in the form of triangles. A Comparison Example carried out in the usual way with an LHSV of 0.72 is characterized by squares. It can be seen that the life of the catalyst is not significantly shortened by the process according to the invention.

Figure 2:
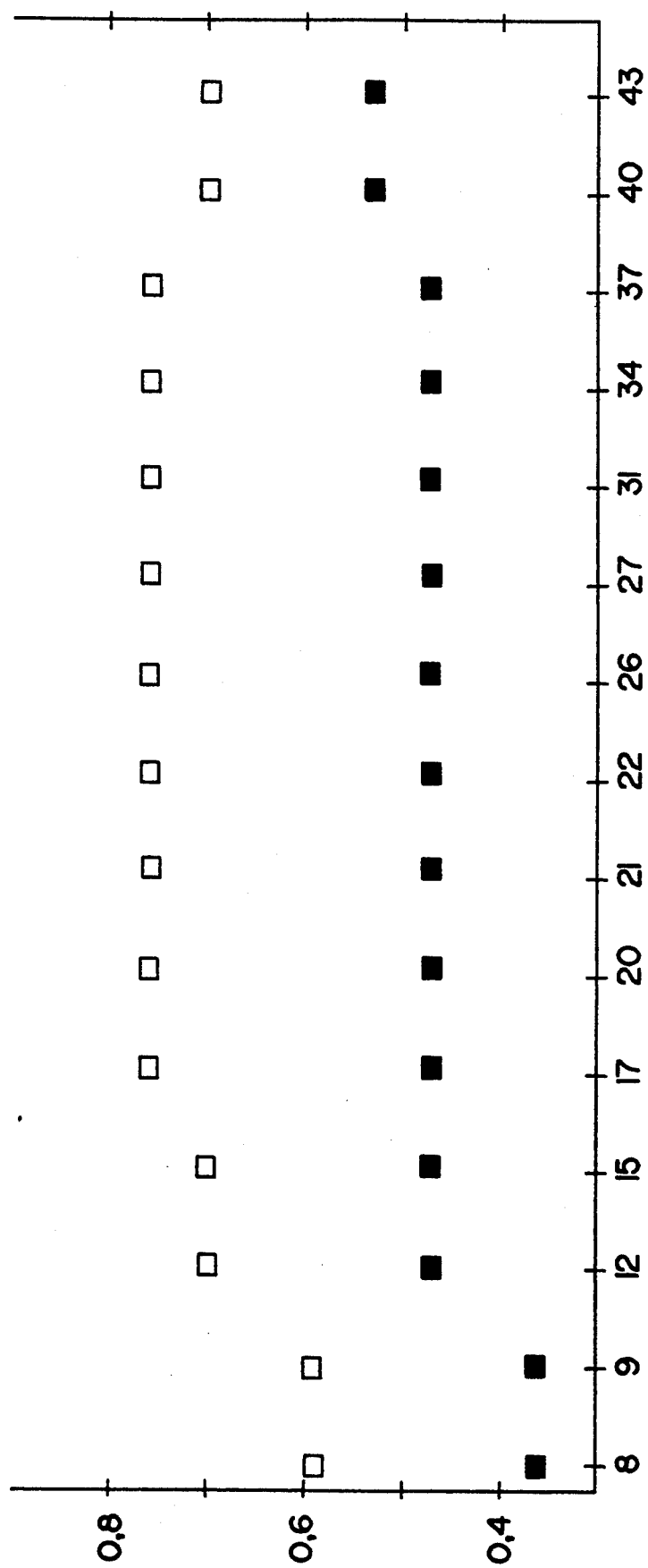
FIG. 2 shows the catalyst load expressed in LHSV and plotted against the operating time in days in the direct hydrogenation of coconut oil.

FIG. 2 shows the catalyst load for the first reactor in the form of empty squares and for the following reactor, the second reactor, in the form of the filled-in squares. These LHSV values show that high catalyst loads can still be achieved in the following reactor.

Figure 3:
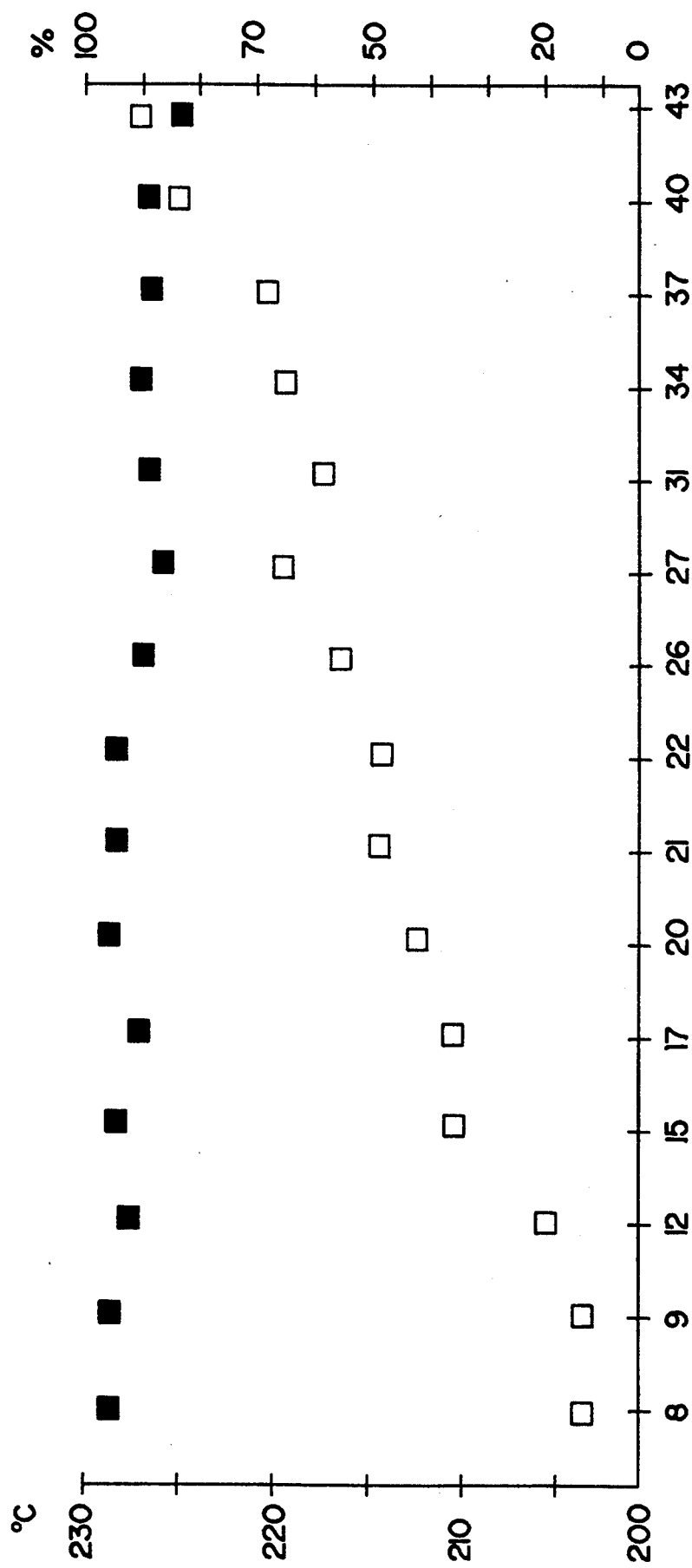
FIG. 3 shows the temperature profile and the yield of 1,2-propanediol in the direct hydrogenation of coconut oil plotted against the operating time in days.
Figure 4:
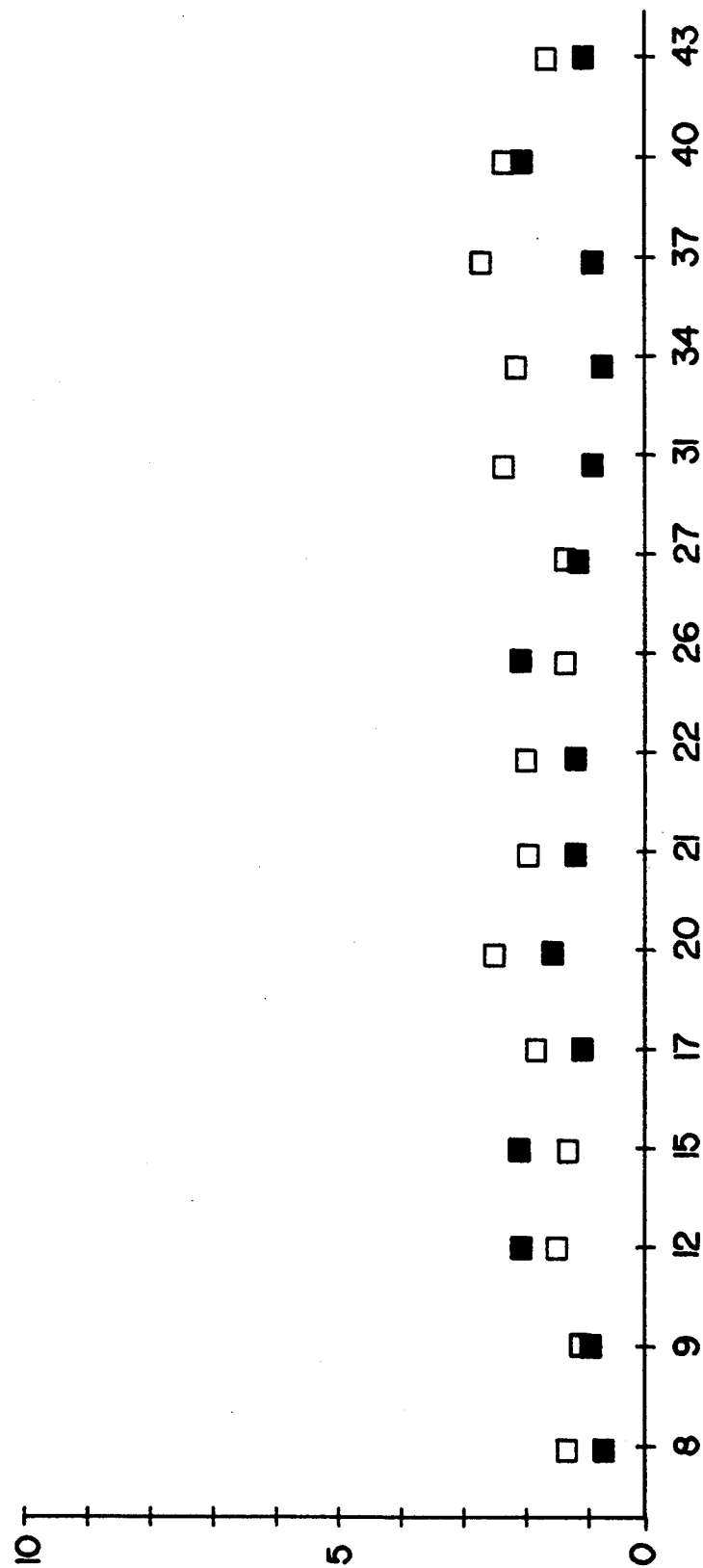
FIG. 4 shows the saponification value in this direct hydrogenation likewise plotted against the operating time in days.

In FIG. 3, the temperature is represented by the empty squares and the yield of 1,2-propanediol by the filled-in squares. A good yield is obtained, even after a prolonged period of operation. This is also clear from FIG. 4 in which the saponification value for the first reactor is represented by the empty squares and, for the second reactor, by the filled-in squares.

Further particulars of the embodiments can be found in Table 1.

Figure 5:
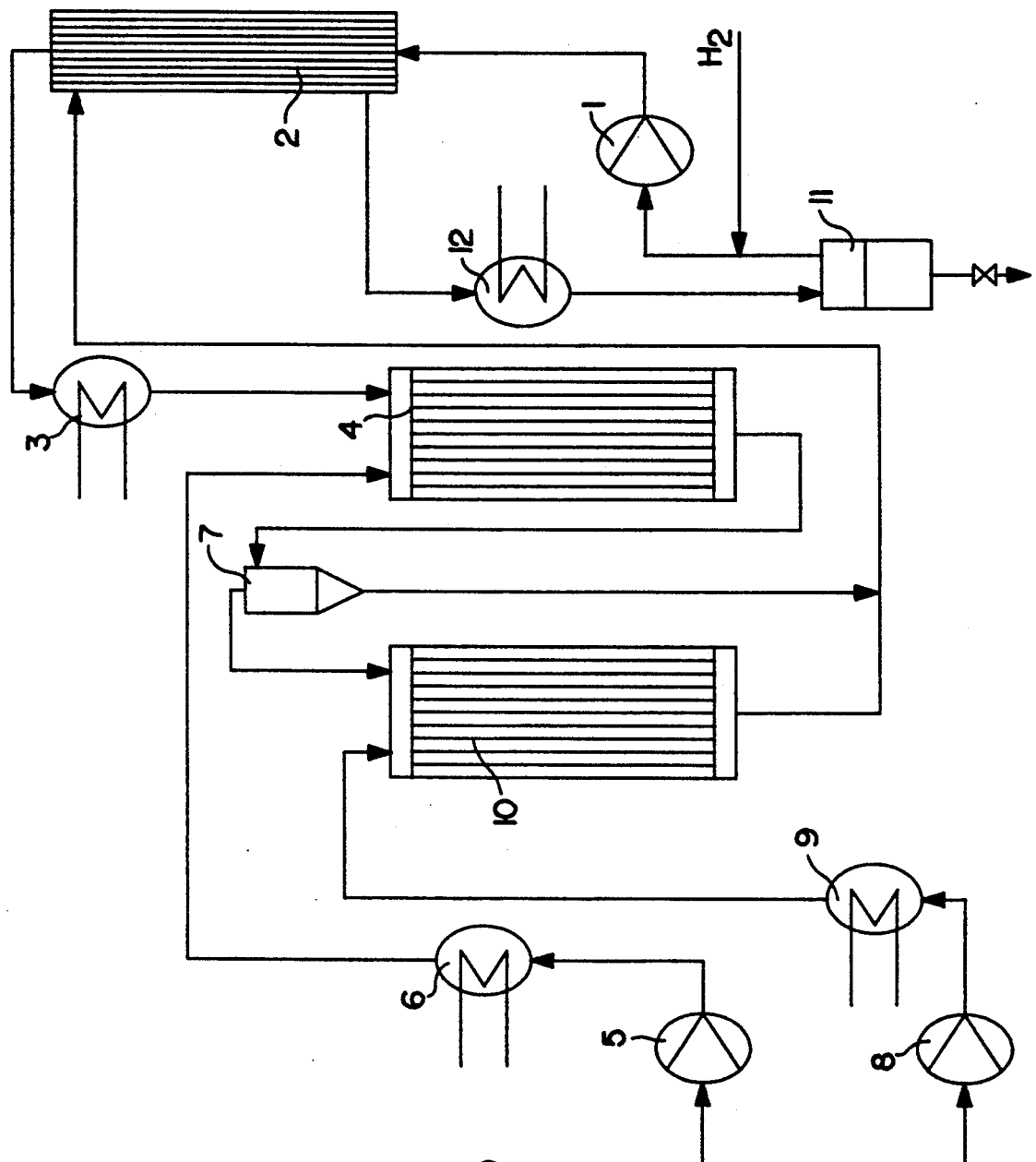
FIG. 5 diagrammatically illustrates one embodiment of the plant according to the invention.

FIG. 5 diagrammatically illustrates the arrangement of the reactors. A gas recirculation pump 1 feeds fresh hydrogen together with recycled hydrogen through the countercurrent heat exchanger 2 and the peak heater 3 to the first reactor 4. At the same time, the pump 5 pumps the starting material into the reactor 4 via the heater 6. The hot reaction gas is freed from the liquid reaction product in the centrifugal separator 7 and, together with the starting material, is passed through the second reactor 10 via the pump 8 and the heater 9. Liquid and gaseous reaction products are introduced into the high-pressure separator 11 through the countercurrent heat exchanger 2 and the cooler 12. The reaction gas is compressed together with the fresh hydrogen in the compressor 1 and recirculated.

TABLE 1

| | Catalyst type: CuCr | | |
| | Catalyst form: 3 mm extrudate | | |
| Reactor | 1 | 2 | 1 + 2 |
|---|---|---|---|
| Pumice stones, botton | 500 ml | 500 ml | 1000 ml |
| Quantity of catalyst | 21.04 kg | 20.94 kg | 41.98 kg |
| Catalyst volume | 17.53 l | 17.44 l | 35 l |
| Charging | Vibrating chute | Vibrating chute | Vibrating chute |
| Charging time | 5 mins. | 5 mins. | |
| Dust component | 2.40% | 0.98% | 1.68% |
| Pumice stones, top | 100 ml | 100 ml | 200 ml |
| Empty volume | 200 ml | 200 ml | 400 ml |

The starting data and results of the hydrogenation of fatty acid methyl ester in accordance with the invention are shown in the following Table.

| Particulars of starting material | |
|---|---|
| $C_{12-18}$ fatty acid methyl ester (dist.) from palm kernel oil | |
| Characteristic data | saponification value: 224 iodine value: 16 |
| Reactor data | |
| Reactor volume | 2 × 20 l double-tube plant |
| Length | 2 × 6 m |
| Reaction data | |
| Reaction temperature | 185° C. |
| Reaction pressure | 250 bar |
| LHSV | 0.5 $(h^{-1})$ |
| Quantity of hydrogen recycle gas | 2.0 cbm/h (at 250 bar/60° C.) |
| Reaction product data | |
| $C_{12-18}$ fatty alcohol/ methanol mixture | |
| Analysis data (after removal of methanol) | |
| Saponification value | reactor 1: 0.2 reactor 2: 0.3 |

The iodine values of both samples were below 1; the hydrocarbon content was below 0.2% by weight.

We claim:

1. A process for hydrogenation of a fatty material to a fatty alcohol, wherein a liquid fatty material is contacted with a stoichiometric excess of hydrogen at an elevated temperature and pressure, in the presence of a fatty material hydrogenation catalyst, in a fixed-bed reactor, to form liquid reaction product which comprises: introducing a liquid fatty material feed directly into at least two fixed-bed reactors; and passing the hydrogen, in a 10 to 100 fold stoichiometric excess in relation to the fatty material, into the at least two reactors in series, without cooling the hydrogen between the at least two reactors.

2. A process of claim 1 wherein the process is carried out in two reactors.

3. A process of claim 1, wherein the liquid reaction product is separated from the gas issuing from a preceding reactor before the gas enters a following reactor.

4. A process of claim 3 wherein the liquid reaction product, separated from the gas, is introduced into the gas issuing from the last reactor, in the series, the gas and liquid are cooled, separated into a liquid phase and a gas phase and the gas phase is returned to the first reactor.

* * * * *